United States Patent [19]

Ueno

[11] Patent Number: 5,246,964

[45] Date of Patent: Sep. 21, 1993

[54] TREATMENT OF INFLAMMATORY DISEASES WITH POLYOXYETHYLENESORBITAN MONO-HIGHER-FATTY ACID ESTERS

[75] Inventor: Ryuji Ueno, Hyogo, Japan

[73] Assignee: K.K. Ueno Seiyaku Oyo Kenkyujo, Osaka, Japan

[21] Appl. No.: 726,673

[22] Filed: Jul. 8, 1991

[30] Foreign Application Priority Data

Jul. 10, 1990 [JP] Japan .................................. 2-184964

[51] Int. Cl.$^5$ ............................................. A61K 31/34
[52] U.S. Cl. .................................... 514/473; 514/886; 514/887; 514/914
[58] Field of Search ................ 514/473, 886, 887, 914

[56] References Cited

PUBLICATIONS

*Proceedings of the Society for Experimental Biology and Medicine*, vol. 184, No. 4, 1987, pp. 477–482.

*Primary Examiner*—Frederick E. Waddell
*Assistant Examiner*—Kimberly R. Jordan
*Attorney, Agent, or Firm*—Sughrue, Mion, Zinn, Macpeak & Seas

[57] ABSTRACT

A method of treatment of inflammatory diseases which comprises administering, to a subject in need of such treatment, an anti-inflammatory effective amount of a polyoxyethylenesorbitan mono-higher-fatty acid ester.

10 Claims, No Drawings

TREATMENT OF INFLAMMATORY DISEASES WITH POLYOXYETHYLENESORBITAN MONO-HIGHER-FATTY ACID ESTERS

BACKGROUND OF THE INVENTION

1. Field of the Invention

The present invention relates to a treatment of inflammatory diseases with polyoxyethylenesorbitan mono-higher-fatty acid esters which have been used as surfactants.

2. Background Information

It is well known that polyoxyethylenesorbitan mono-higher-fatty acid esters can be used as surfactants for emulsifying or dispersing purpose. It is also known that polyoxyethylenesorbitan monooleate (also known as Polysorbate 80) is a substance inducing the release of histamine (Agents and Actions, 16, 470-477).

As a result of extensive studies about the biological properties of polyoxyethylenesorbitan mono-higher-fatty acid esters, the present inventor have discovered that these compounds are useful as an agent for treating inflammatory diseases.

SUMMARY OF THE INVENTION

In a first aspect, the present invention provides a method for treatment of inflammatory diseases which comprises administering, to a subject in need of such treatment, an anti-inflammatorily effective amount of a polyoxyethylenesorbitan mono-higher-fatty acid ester.

In a second aspect, the present invention provides a use of polyoxyethylenesorbitan mono-higher-fatty acid ester for the manufacture of a medicament for treatment of inflammatory diseases.

In a third aspect, the present invention provides a pharmaceutical composition for treatment of inflammatory diseases comprising a polyoxyethylenesorbitan mono-higher-fatty acid ester in association with a pharmaceutically acceptable carrier, diluent or excipient.

DETAILED DESCRIPTION OF THE INVENTION

The term "inflammatory disease" means lesions caused by a defensive reaction or an inflammatory reaction of a living body against harmful influence of circumstances (such as physical, chemical and biological circumstances) having signs of redness, heat, pain, swelling and loss of function.

The term "anti-inflammatory" means a tendency or an ability to act against or protect from or inhibit the inflammatory reaction. The polyoxyethylenesorbitan mono-higher-fatty acid esters used in the instant invention have such tendency or ability.

The inflammatory diseases includes conjunctivitis, iritis, uveitis, central retinitis, external otitis, acute suppurative otitis media, mastoiditis, labyrinthitis, chronic rhinitis, acute rhinitis, sinusitis, pharyngitis, tonsillitio, chronic bronchitis, acute bronchilotis, lobar pneumonia, bronchopneumonia, primary atypical pneumonia, dry pleurisy, wet pleurisy, mediastinitis, acute rheumatic endocarditis, bacterial endocarditis, thrombophlebitis, polyarteritis, acute nephritis, chronic nephritis, cystitis, paranephlitis, stomatitis, esophagitis, acute gastritis, chronic gastritis, ulcertive colitis, acute appendicitis, chronic hepatitis, acute hepatitis, cholangiolitic hepatitis, cholecystitis, chronic pancreatitis, acute pancreatitis, chronic peritonitis, acute peritonitis, thyroiditis, contact dermatitis, acute hemorrhagic encephalitis, purulent meningitis, optic neuromyelitis, alcohlic polyneuritis, diabetic polyneuritis, polymyositis, myositis ossificans, degenerative arthritis, rheumatoid arthritis, periarthritis scapulohumeralis, osteitis deformans, etc.

The polyoxyethylenesorbitan mono-higher-fatty acid esters used in the present invention are mono ester of polyoxyethylenesorbitan with higher-fatty acids, said polyoxyethylenesorbitan being formed by reacting sorbitan with ordinarily 15 to 25 molar excess and preferably about 20 molar excess of ethylene oxide, and may contain a little amount of di- or tri-esters. The above molar number of ethylene oxide is represented in round brackets.

The higher-fatty acids include fatty acids having 10 to 24 and preferably 12 to 20 carbon atoms. Such acids include saturated fatty acids and unsaturated fatty acids. As the saturated fatty acids, lauric acid, myristic acid, palmitic acid, stearic acid arachidic acid, etc. are preferred. Polyoxyethylene(20)sorbitan monolaurate is known as Polysorbate 20 and commercialized under the tradename Tween 20. Polyoxyethylene(20)sorbitan monopalmitate is known as Polysorbate 40 and commercialized under the tradename Tween 40. Polyoxyethylene(20)sorbitan monostearate is known as Polysorbate 60 and commercialized under the tradename Tween 60. As the unsaturated fatty acids, myristoleic acid, palmitoleic acid, oleic acid, gadoleic acid, linoleic acid etc. are preferred. Polyethylene(20)sorbitan monooleate is known as Polysorbate 80 and commercialized under the tradenames Sorlate, Tween 80, Monitan and Olothorb.

Since the polyoxyethylenesorbitan mono-higher-fatty acid esters have action inhibiting inflammatory reaction, they are useful in treatment of inflammatory disease. The above compounds may be used as a medicine for animals and humans. Although the principal route is topical, the administration of the above compounds is not limited thereto and various other routes may be possible. While the dosage will vary depending on the animal or human patient, age, body weight, symptom to be treated, desired therapeutic effect, route of administration, term of treatment and the like, satisfactory effects will be obtained with the dosage of 0.01–100 μg/eye administered locally (i.e. ocutarly) or 0.001–500 mg/kg administered in 2 to 4 divided doses a day or as a sustained form.

The above compounds is usually administered in the form of a pharmaceutical composition containing at least one of said compounds and optionally other ingredients conveniently used, such as carrier, diluent or excipient. The composition includes liquids such as a solution, an emulsion and a suspension, or semi-solids such as gel and ophthalmic ointment.

Diluents for the aqueous solution or suspension includes, for example, distilled water an physiological saline. Diluents for the nonoaqueous solution and suspension include, for example, vegetable oils e.g. olive oil, liquid paraffin, mineral oil, and propylene glycol and p-octyldodecanol. The composition may also contain isotonization agents such as sodium chloride, boric acid, sodium citrate, etc. to make isotonic with the lacrimal fluid and buffering agents such as borate buffer, phosphate buffer, etc. to maintain pH about 5.0 to 8.0. Further, stabilizers such as sodium sulfite, propylene glycol, etc., chelating agents such as sodium edetate, etc., thickeners such as glycerol, carboxymethylcellulose, carboxyvinyl polymer, etc. and preservatives such as methyl paraben, propyl paraben, benzalkonium chloride, cetylpyridinium chloride, chlorobutanol, etc. may also added. These can be sterilized e.g. by passing through a bacterial filter or by heating.

The ophthalmic ointment may contain vaseline, Plastibase, Macrogol etc. as a base and surfactant for increasing hydrophilicity. It may also contain geling agents such as carboxymethylcellulose, methylcellulose, caboxyvinyl polymer, etc.

In addition, the composition may contain antibiotics such as chloramphenicol, penicilin, etc. in order to prevent or treat bacterial infection.

A more complete understanding of the present invention can be obtained by reference to the following Formulation Examples and Test Examples which are provided herein for purpose of illustrating only and are not intended to limit the scope of the invention.

FORMULATION EXAMPLE 1

| | | |
|---|---|---|
| polyoxyethylene (20) sorbitan monooleate (polysorbate 80) | | 1.0 g |
| sodium chloride | | 0.8 g |
| distilled water | q.s. to | 100 ml |

TEST EXAMPLE 1

The composition of Formulation Example 1 was topically administered to both eyes of mice at a dose of 5 µl per eye. Three minutes after the administration, 0.5% Evans Blue in physiological saline (0.5 ml) was injected in the caudal vein. Immediately after, 0.01% histamine in physiological saline (50 µl) was injected subconjunctivally at an upper eyelid. After 30 minutes, the animals were sacrificed by vertebral cervial dislocation and the scalp was peeled away towards the eyelid. Part of skin and conjunctive showing inflammation was cut off and weighed.

Then, said conjunctive was minced and extracted overnight with 4 ml formaldehyde at 40° C. with shaking. The dye in the conjunctive was assayed by measuring absorption of the extract at 625 nm.

The results are shown in Table 1.

TABLE 1

| | Number of Animals | Weight of conjunctive (Mean ± S.D.) | Dye (µg/part) |
|---|---|---|---|
| Control | 26 | 38.2 ± 1.8 | 5.59 ± 0.36 |
| Formulation Example 1 | 24 | 36.8 ± 1.4 | 4.76 ± 0.22* |

*T-Test, $P < 0.1$

The above results show that the tested compound has an activity inhibiting experimental inflammation.

What is claimed is:

1. A method of treatment of inflammation which comprises administering, to a subject in need of such treatment, an amount effective for treating inflammation of a polyoxyethylenesorbitan mono-higher-fatty acid ester.

2. The method according to claim 1, in which the higher-fatty acid is a fatty acid having 10 to 24 carbon atoms.

3. The method according to claim 1, in which the polyoxyethylenesorbitan is formed by reacting sorbitan with 15 to 25 moler excess of ethylene oxide.

4. The method according to claim 1, in which the higher-fatty acid is unsaturated.

5. The method according to claim 1, in which the polyoxyethylenesorbitan mono-higher-fatty acid ester is polyoxyethylene(20)sorbitan mono oleate.

6. The method according to claim 1, in which the polyoxyethylenesorbitan mono-higher-fatty acid ester is topically administered.

7. The method according to claim 1, wherein the inflammation associated with conjunctivitis, iritis, uveitis, central retinitis, external otitis, acute suppurative otitis media, mastoiditis, labyrinthitis, chronic rhinitis, acute rhinitis, sinusitis, pharyngitis, tonsillitis, chronic bronchitis, acute bronchiolitis, lobar pneumonia, bronchopneumonia, primary atypical pneumonia, dry pleurisy, wet pleurisy, mediastinitis, acute rheumatic endocarditis, bacterial endocarditis, thrombophlebitis, polyarteritis, acute nephritis, chronic nephritis, cystitis, paranephlitis, stomatitis, esophagitis, acute gastritis, chronic gastritis, ulcertive colitis, acute appendicitis, chronic hepatitis, acute hepatitis, cholangiolitic hepatitis, cholecystitis, chronic pancreatitis, acute pancreatitis, chronic peritonitis, acute peritonitis, thyroiditis, contact dermatitis, acute hemorrhagic encephalitis, purulent meningitis, optic neuromyelitis, alcoholic polyneuritis, diabetic polyneuritis, polymyositis, myositis ossificans, degenerative arthritis, rheumatoid arthritis, periarthritis scapulohumeralis or osteitis deformans is treated.

8. The method according to claim 1, wherein the inflammation treated affects the eye.

9. The method according to claim 7, wherein conjunctivitis, iritis, uveitis or central retinitis is treated.

10. The method of claim 7, wherein conjunctivitis is treated.

* * * * *